United States Patent [19]

Ranney

[11] Patent Number: 5,108,759
[45] Date of Patent: * Apr. 28, 1992

[54] ENDOTHELIAL ENVELOPMENT DRUG CARRIERS

[76] Inventor: David F. Ranney, 3539 Courtdale Dr., Dallas, Tex. 75234

[*] Notice: The portion of the term of this patent subsequent to May 15, 2007 has been disclaimed.

[21] Appl. No.: 448,121

[22] Filed: Dec. 8, 1989

Related U.S. Application Data

[62] Division of Ser. No. 33,432, Apr. 1, 1987, Pat. No. 4,925,678.

[51] Int. Cl.$^5$ .............. A61K 9/16; A61K 45/05; A61K 9/50; A61K 37/22
[52] U.S. Cl. .............. 424/493; 424/7.1; 424/9; 424/85.2; 424/450; 424/460; 424/461; 424/463; 424/469; 424/488; 424/499; 428/402.2; 428/402.24; 436/829; 514/963; 514/965
[58] Field of Search .............. 424/7.1, 9, 85.2, 450, 424/460, 461, 463, 469, 488, 499; 428/402.2, 402.24; 436/829; 514/963, 965

[56] References Cited

U.S. PATENT DOCUMENTS

4,904,479 2/1990 Illum .............. 424/469

FOREIGN PATENT DOCUMENTS

| | | |
|---|---|---|
| 1168150 | 5/1984 | Canada . |
| 0087786 | 9/1983 | European Pat. Off. . |
| WO83/03426 | 10/1983 | European Pat. Off. . |
| WO84/00294 | 2/1984 | European Pat. Off. . |
| 0167825 | 1/1986 | European Pat. Off. . |
| 0240424 | 10/1987 | European Pat. Off. . |
| 1516348 | 7/1978 | United Kingdom . |
| 2041517 | 9/1980 | United Kingdom . |
| 2185397 | 7/1987 | United Kingdom . |

OTHER PUBLICATIONS

European Search Report, Oct. 14, 1988.
Ranney, D. F., Biochem. Pharmacol., vol. 35 (1986) 1063-1069.

Primary Examiner—Thurman K. Page
Assistant Examiner—Carlos Azpuru
Attorney, Agent, or Firm—Arnold, White & Durkee

[57] ABSTRACT

This application describes the preparation and in vivo testing of surface coatings and matrix materials, which when applied to or caused to comprise the carriers for drugs and diagnostic agents, and administered in a fashion that allows efficient vascular access, causes the carriers to recognize determinants present or normal or focally diseased endothelium, and induces the following in vivo effects: 1) rapid, partial or total endothelial envelopment of the drug (diagnostic) carrier; 2) sequestration of the carrier and protecting entrapped agent from blood vascular clearance at an early time (2 minutes) when the endothelial pocket which envelops the carrier still invaginates into the vascular compartment; 3) acceleration of the carrier's transport across or through the vascular endothelium and/or subendothelial structures into the tissue compartment (interstitium); and 4) improvement of the efficiency with which the drug (or diagnostic) carrier migrates across the endothelium, or epi-endothelial or subendothelial barriers, such that a lower total drug dose is required to obtain the desired effect relative to that required for standard agents.

11 Claims, 6 Drawing Sheets

ENDOTHELIAL ENVELOPMENT DRUG CARRIERS

This is a divisional application of copending application Ser. No. 033,432, filed Apr. 1, 1987 and incorporated by reference herein now U.S. Pat. No. 4,925,678.

BACKGROUND OF THE INVENTION

Until recently, the localization of intravascular drugs in body tissues has depended on chemical partitioning across microvascular barriers into the tissue compartments of multiple body organs. This resulted in only 0.01% to 0.001% of the injected dose actually reaching the intended targets. Approximately 20 years ago, drugs were entrapped in liposomes and microspheres. This modified the initial biodistributions and redirected them to phagocytes in the reticuloendothelial organs: liver, spleen and bone marrow. In 1978, the present inventor and coworkers developed a means to co-entrap drug plus magnetite in microspheres which could be injected intravenously and localized magnetically in the tissue compartments of nonreticuloendothelial target organs (e.g., lung and brain). Magnetic capture was accomplished by selective dragging of the particles through the vascular endothelium into normal tissues and tissue tumors positioned adjacent to an extracorporeal magnet of sufficient strength (0.5 to 0.8 Tesla) and gradient (0.1 Tesla/mm). Although this technique was highly efficient and deposited between 25% and 50% of an injected dose in the desired target tissue, it was also a very complicated approach which had the following major disadvantages: 1) restriction of use to specialized medical centers; 2) permanent disposition of magnetite in target tissue; 3) focal overdosing of drug due to inhomogeneity of the capturing magnetic field; and 4) application to a very limited number of therapeutic agents. In the process of studying magnetic targeting, however, it was learned that slow (controlled) release of toxic drugs from entrapment-type carriers (microspheres) protected the normal cells within the local tissue environment from drug toxicity and still gave effective treatment of tumor cells and microorganisms. At the time when monoclonal antibodies became generally available for animal and clinical research, it was hoped that antibody-drug conjugates would limit the biodistribution of toxic agents and cause them to become deposited in foci of disease (tumors and infections) which were located across the microvascular barrier within target tissues. Unfortunately, most monoclonal antibodies were (and are still) obtained from mice, making them foreign to human recipients. Conjugation of drugs at therapeutically relevant substitution ratios makes the derivatives even more foreign and impairs their binding specificities. Hence, antibody-drug conjugates are cleared rapidly by the liver, in a fashion similar to that for liposomes. Importantly, their localization in most solid tumors is even further impaired by the presence of a partially intact microvascular barrier which separates the tumor tissue (interstitium) from the bloodstream. This allows only about 1% to 7% (at best) of the injected dose to reach nonreticuloendothelial targets. Selected lymphomas and leukemias provide exceptions to this rule because of a greater natural breakdown of this vascular barrier. However, for the vast majority of solid tumors and infections, a general-purpose method is still needed to deliver drugs efficiently across microvascular barriers in a depot (controlled release) form. This depot form of drugs is necessary in order to protect vascular endothelium and normal tissue cells from the toxic effects of drugs, protect drug from endothelial and tissue metabolism during transit, and make drug bioavailable at a controlled therapeutic rate within the target tissues and tissue lesions.

Active endothelial transport has been demonstrated for small molecules (e.g., glucose and insulin), however, no studies other than that of the present inventor. Present examples show that transendothe migration of particles and molecular aggregates larger than about 2 nm. in diameter are accelerated by the application of surface coatings which bind multiply to receptors or antigens which are either synthesized by endothelium or are synthesized at other sites but become tightly associated with the endothelial surface. (Ranney, Biochem. Pharmacology, V. 35, No. 7, pp. 1063-1069 (1986)).

SUMMARY OF THE INVENTION

The present invention involves a composition of matter comprising a carrier having a surface, at least two molecules of drug or diagnostic agent contained by the carrier and a multivalent binding agent specific for endothelial surface determinants. At least a portion of said binding agent is attached to the surface of the carrier. The carrier preferably has a size of between about 25 nm and about 250 um. The binding agent is one which bioadheres to endothelial surface determinants and induces envelopment of the carrier by endothelial cells of a vascular wall and transfer across said wall to proximal tissues. The term bioadhere as used herein means interactions characteristically encountered in biological systems involving multiple molecular and usually noncovalent bonds.

The carrier involved in the method and composition of matter of the present invention preferably comprises one or more of macromolecules, microaggregates, microparticles, microspheres, nanospheres, liposomes and microemulsions. The endothelial surface determin-ants those characteristic of endothelial tissues, some of which may be defined further as being enhanced in quantity when proximal to tissue lesions. These endothelial surface determinants comprise, for example, Factor VIII antigen, Interleukin I receptor, endothelial thrombodulin, endothelial tissue factor, subendothelial tissue moieties, fibrin D-D dimer and GP 2b/3a glycoprotein complex.

The multivalent binding agent of the present invention may preferably be a substance such as heparin, a heparin fragment or Ulex Europaius I lectin. In certain cases an antibody directed toward endothelial surface antigens may be utilized as the multivalent binding agent. The multivalent binding agent of the present invention may also be directed toward subendothelial tissue moieties such as laminin, type IV collagen, fibronectin or a fragment chemotactic for monocytes. These subendothelial moieties may, for example because of lesion formation, be exposed to vascular fluids and thus bind and/or envelop the composition of matter of the present invention. The composition of matter of the present invention may comprise a multivalent binding agent which binds to vascular endothelium via endothelial surface receptors, surface enzymes, substances which coat the endothelial surface or substances which immediately underly the endothelium and may be deposited, exposed or altered in normal vascular endothelium or proximal to foci of tissue or endothelial disease.

The composition of matter of the present invention generally involves binding of a sample thereof to endothelia and an induction of the endothelia to totally or partially envelop bound sample in less than 10 to 15 minutes. The interaction of the composition of matter of the present invention with endothelia may produce an induction of the endothelia to undergo transient separation or opening, thereby exposing subendothelial determinants for which the composition of matter has binding affinity. The composition of matter of the present invention may by interaction of a sample thereof with endothelia produces an induction of total or partial sequestration of the associated drug or diagnostic agent at an early time when it still resides in or protrudes into an associated vascular lumen.

The composition of matter of the present invention may be characterized by the interaction of a sample thereof with endothelia which produces an acceleration of transport of the sample across at least one of associated vascular endothelia and subendothelial structures into a proximal tissue compartment. The interaction of a sample of the composition of matter of the present invention with endothelia may result in improvement of the efficiency with which an associated drug or diagnostic agent migrates across the endothelia and associated structures such that a reduced total dose of drug or diagnostic agent may be administered to obtain effects comparable to a significantly higher dose of free drug or diagnostic agent. The interaction of a sample of the composition of matter of the present invention with endothelia may produce an induction of total or partial sequestration of the drug or diagnostic carrier at an early time when it still resides in or protrudes into an associated vascular lumen.

The composition of matter of the present invention may preferably be a microsphere in certain embodiments. Such a microsphere comprises a matrix and is most preferably between 0.2 and 250 um in diameter. The matrix is preferably a carbohydrate and may be a carbohydrate such as heparin which also has multivalent binding capabilities. Dextran is also a preferred matrix and may preferably be coated with a multivalent binding agent such as heparin, for example. In this latter case the composition of matter of the present invention is preferably about 10 % (w/w) heparin.

A drug or diagnostic agent comprised in the composition of matter of the present invention may be the antifungal agent amphotericin B. The amphotericin B or other hydrophobic drug or diagnostic agent may be in a complex. The drug or diagnostic agent such as amphotericin B may be in a controlled-release form, for example within internally entrapped micelles of pluronic G68 block copolymer, polyoxypropylene-polyoxyethylene.

The composition of matter of the present invention may preferably comprise a microsphere carbohydrate matrix and, as a multivalent binding agent. an exposed or covert lectin capable of binding endothelial surface determinants, enzymes, epi-endothelial or subendothelial substances.

The composition of matter of the present invention, in one preferred embodiment, comprises a carrier having a surface, at least two molecules of drug or diagnostic agent contained by the carrier, a multivalent binding agent specific for endothelial determinants, at least a portion of said binding agent being attached to the surface of said carrier and a removable coating which renders the multivalent binding agent unexposed to external contacts. The removable coating is a coating subject to removal by a triggering event. The triggering event is a condition such as lowered pH, temperature alteration, contact with normal endothelia, contact with abnormal endothelia, altered enzyme levels or physical changes induced by application of external forces such as radiofrequency, ultrasound, magnetism or electricity.

The composition of matter of the present invention, with or without a removable coating may be one in which the multivalent binding agent is a lectin with affinity for endothelial, epi- or subendothelial determinants. In one preferred embodiment the lectin is Ulex Europaeus I lectin and the removable coating is fucose, fucosyl albumin or albumin-fucosyl amine.

The composition of matter of the present invention may comprise a multivalent binding agent which is an antibody with affinity for endothelial or subendothelial binding sites. The multivalent binding agent of the present invention also may be a substrate for an endothelial or epi-endothelial enzyme; a peptide, for example benzoyl-phenyalanyl-alanylproline, which has a substrate affinity for endothelial angiotensin converting enzyme.

In another preferred embodiment of the present invention, the drug or diagnostic agent and the multivalent binding agent are the same and comprise a molecular microaggregate of 3 to 200 nanometers in molecular diameter, most preferably where the drug or diagnostic agent and the multivalent binding agent are the same and comprise a molecular microaggregate of heparin of about 100 to 200 nanometers in molecular diameter.

The composition of matter of the present invention are, in a preferred embodiment, in a pharmaceutically acceptable solution suitable for intravascular or other parenteral injection.

Methods of use of the composition of matter of the present invention comprise administration to an animal of a carrier having a surface, at least two molecules of drug or diagnostic agent contained by the carrier and a multivalent binding agent specific for endothelial surface determinants, at least a portion of said binding agent being attached to the surface of said carrier as described above. The above composition of matter is preferably contained in a pharmaceutically acceptable carrier. The multivalent binding agents are selected for the particular targeted sites, most especially the epithelia. The drug or diagnostic agent is selected according to the particular lesion being treated or the diagnostic method being utilized. The carrier may be a natural or synthetic polymer.

BRIEF DESCRIPTION OF THE DRAWINGS

FIG. 1 is a lung tissue section stained with PAS, which is representative of the test mice sacrificed 2–5 minutes after intravenous injection of the unheated, acetone-stabilized heparin microspheres.

FIG. 2 is a lung tissue section stained with PAS, which is representative of the test mice sacrificed 10 minutes after intravenous injection of the same heparin microspheres as in FIG. 1.

FIG. 3 is a lung tissue section stained with PAS, which is representative of the test mice sacrificed 2–5 minutes after intravenous injection of the fucose-blocked, Ulex Europaeus agglutinin I-coated spheres of Example 4.

FIG. 4 is a lung tissue section stained with a reticulin stain, which is representative of the test mice sacrificed at 10 minutes after intravenous injection of the identical fucose-blocked, Ulex Europaeus agglutinini-coated spheres of Example 3.

FIG. 5 is a lung tissue section stained with PAS, which is representative of the test mice sacrificed 20 minutes after intravenous injection of the identical fucose-blocked spheres of Examples 3 and 4.

FIG. 6 is a representative example of control microsphere ($M_C$) of plain agarose which is present within a lung microvessel (V) 10 minutes after intravenous injection.

DESCRIPTION OF THE PREFERRED EMBODIMENT

Figure 1:

The present invention involves nontoxic, biodegradable small microspheres (less than about 4-100 micrometers (um) in size) and microaggregates (100-200 micrometers, nm) comprising (or coated with) endothelialbinding substances. These substances induce the following serial steps upon intravenous injection of particles into test rodents: 1) endothelial bioadhesion; 2) rapid (2-minute) endothelial envelopment (partial or total) of the particles (microaggregates); 3) a facilitated (accelerated) migration of intact drug-carrier particles across microvessels into the tissue compartment; (which is largely complete within 10 to 20 minutes of injection); and 4) delayed release of drug (or diagnostic agent) from a microsphere formulation of envelopment carrier which is known to correlate with controlled bioavailability of drug within the target tissue (lesion) in vivo.

The examples presented herein include three major approaches for compositions of matter serving as formulation carriers for efficient, nonmagnetic drug localization in normal and diseased tissues, either in the presence or absence of potentially competing receptors on the surfaces of circulating red cells, white cells or platelets. These approaches are as follows: 1) microparticles (and microaggregates) comprising (and coated with) heparins which bind to the complementary heparins and heparin sulfates present on normal endothelium throughout the body (lung and brain binding are documented below); 2) microparticles with surface-conjugated Ulex Europaeus agglutinin I, a glycoprotein which binds to factor VIII antigen present on the luminal surface of endothelium and which is reported to be present at increased densities in foci of disease (Loesberg et al., *Biochem. Biophys. Acta*, V. 763, pp. 160 (1983)); 3) microparticles with surface-conjugated Ulex Europaeus agglutinin I, in which the factor VIII antigen-binding site is of the Ulex agglutinin blocked noncovalently by addition of the sugar hapten, L-fucose, in order to render this site covert (reversibly coated) and prevent its binding of potentially similar receptors on circulating red blood cells. Surface-coated microcarriers may also make use of interleukin 1 and its receptor sites induced by disease on the surface of vascular endothelium (Libby et al., *Fed. Proc.*, V. 45, p. 1074 (1986)).

For these examples, initial morphometric data indicated that at least 25% of the injected carrier migrated across microvessels of the first target organ encountered, namely, lungs by the intravenous route, and brain by the carotid arterial route. Hence, these new carriers are (by a factor of five) the most efficient general-purpose drug delivery devices described. In one example, microparticles (0.1 to 0.6 um) of amphotericin-cyclodextrin which released the drug at a very slow rate (t ½ greater than about 36 hours) were entrapped within larger (5 to 25-um) macroparticles of a more rapidly degrading heparin matrix (t ½ about 15-minutes in flowing blood and blood amylase). Such a hybrid microcarrier allows for both slow release of the extravascular drug within tissues and rapid degradation of the fragments remaining within microvessels. The latter property minimizes transient disruption of microvascular blood flow which might otherwise occur upon infusion of therapeutically relevant doses of the microcarrier. This formulation comprises a true "cellular drug carrier" because it mimics the morphology and function of white blood cells (living macroparticles), which migrate into tissue lesions and release lysosomal enzymes and lymphokines (biopharmaceuticals) as a controlled rate from their intracellular granules (living microparticles).

From the results of the present invention and known biological functions and relationships involving endothelial and related binding substances, the following extensions of the present technology involving multivalent binding agents and variations thereof appear readily accomplished. These extensions may be grouped as relating to multivalent binding agents as follows:

GROUP I. Substances which bind to native endothelium such as:
1. Heparin
2. Heparan sulfate
3. Heparin fragments and synthetic analogues which bind antithrombin III (pentasaccharide hexasaccharides and oligosaccharides)
4. Ulex Europaens I agglutinin (binds factor VIII antigen)
5. F-met-leu-phe
6. t-boc-leu-phe-leu-phe
7. Benzoyl-phe-ala-pro (BPAP, binds angiotensin converting enzyme)
8. Other inhibitors of angiotensin converting enzyme
9. 5'-nucleotides (bind 5'-nucleotidase)
10. Inactive congeners of the biogenic amines, 5-hydroxytryptamine and norepinephrine
11. Insulin and inactive insulin analogues
12. Transferrin
13. Prostaglandins E, F and stable oligomers
14. Peptide substrates and inhibitors of tissue plasminogen activator (tPA)
15. Albumins and glycosylated albumins
16. Cationic ferritin
17. Low density lipoproteins (LDL)
18. Hirudin-inhibited thrombin (binds thrombomodulin)
19. Antibodies against (and receptor moleculas for): Surface carbohydrates of:
    1. Central lymph-mode endothelium (MEL-14 and MECA-367 Ab's)
    2. Peripheral lymph-mode-endothelium (MECA-79 Ab)
    3. Panendothelium (MECA-325)
    4. Capillary-level endothelium with organ specificity (e.g., lung, liver, and brain endothelial antibodies)
20. Negatively charged polysaccharides or oligosaccharides such as, for example:
    a. Dextran sulfate
    b. Dermatan sulfate
    c. Chondroitin sulfate, and
    d. Hyaluronic acid GROUP II. Substances which bind preferentially to activated and diseased endothelium
1. Ulex Europaeus I agglutinin
2. Ulex Europaeus I agglutinin, reversibly blocked with:

a. Fucose
b. Fucosyl albumin
c. Albumin-fucosyl amine
d. Other neoqlycoproteins
e. Aminated carbohydrates
3. Cytoadhesion molecules with affinity for activated endothelium:
   a. ICAM-1
   b. LFA-1
   c. Mad-1
   d. P50
   e. VLA molecules
4. Interleukin I
5. Antibodies against (and receptor molecules for):
   a. Endothelial leukocyte adhesion molecule, ELAM (H 4/18 and H 18/7 Ab's)
   b. Endothelial tissue factor, tf
   c. Endothelial-associated, fibrin D-D dimer
   d. Class II histocompatibility antigens, Ia and HLA-Dr
   e. Fd receptors
   f. Mo3e surface antigens
   g. Factor VIII antigen
   h. Glycoprotein IIb
   i. Glycoprotein IIIa
   j. Glycoprotein IIb/IIIa complex
   k. Il-1 receptor of endothelium
   l. "Extra domain" of fibronectin, ED GROUP III. Substances which bind to subendothelial molecules and structures exposed by endothelial activation and disease:
1. Ricinus communis agglutinin I (binds to basement membrane molecules)
2. Antibodies against (and receptor molecules for):
   a. Fibronectin
   b. Fibronectin fragments (e.g., monocyte chemotactic fragment)
   c. Laminin
   d. Intercellular adhesion molecules (e.g., ICAM-a)
   e. Type IV collagen
   f. Basement membrane molecules (anti-GBM antibody).

An additional aspect of the present invention, is the formulation of microcarriers in which the endothelial-binding ligands are themselves coated by an outer protective layer of polymeric fucose derivatives. Such derivatives include, for example, the neoglycoproteins, fucosyl albumin and albumin fucosyl amines. Such protective coatings could be used to achieve semiselective targeting of tissue lesions following systemic intravenous administration of such composite carriers. By appropriate selection of the isoelectric and thermodynamic properties of these surface polymers, selective uncoating could be induced at sites of lowered pH which typically exist in microvessels which supply tumors and sites of chronic infection. Selective uncoating is possible because glycoproteins and other surface polymers each exhibit their lowest solubility at their isoelectric point (pKI) and become increasingly soluble (unstable as surface coatings) as the pH is lowered below the pKI. Hence, the optimal isoelectric point for uncoating polymers in the body is at about blood pH (7.35). According to present art, the rate of such uncoating could be accelerated, for example, by incorporating a triggerable form glucose oxidase in the microcarrier matrix which would generate gluconic acid and further protonate the surface polymer at lowered pH. An important consideration in employing these technologies involves minimizing the rapid reticuloendothelial clearance of particles. Just recently, this has become feasible to accomplish by maintaining a small (ca. 50 nm) particle size and coating the particles with combination hydrophilic-hydrophobic block copolymers, such as the tetronic copolymer P908, the pluronic copolymer F68 and others. A second method for inducing selective uncoating in lesional microvessels, is the use of surface coatings which are degraded by lesional degradative enzymes. These enzymes include serine esterases (e.g., tissue plasminogen activator and other enzymes of the coagulation cascade), and lysosomal enzymes (e.g., acid esterases and beta glucuronidase). A third method for selective uncoating involves the potential sensitivity of protective surfaces to external physical energy, such as occurs with melting of surface lipids by regional hyperthermia and disruption of hardened surface coatings by high-frequency ultrasound.

The endothelial envelopment-transport coatings documented below are adaptable for use with all synthetic and natural, solid (Matrix) and deformable (lipid and hollow) transvascular microcarriers, including microspheres, liposomes, artificial membranes, microvesicles, and hydrophilic and hydrophobic microemulsions, wherein the matrix and/or coating materials may be comprised of carbohydrates, oligo- or monosaccharides, proteins or peptides, lipids, alkyl or alkenyl chains, or biocompatible synthetic polymers. The drug or diagnostic agent carriers of the present invention may vary in complexity, including, for example:

1) single chain polymers;
2) molecular microaggregates in which the molecular carrier/aggregate comprises both the endothelial binding moiety and the backbone for linking pro-drug moieties;
3) complex supramolecular carrier comprising multiple matrix material and/or serial coatings, with a major criterion of novelty being that multiple (two or more) endothelial binding sites are engaged by the carrier material or microcarrier surface in order to activate the endothelial cellular processes required for rapid envelopment (thereby sequestering the spheres from vascular degradation and drug form downstream release during transendothelial migration) and transport of the carrier.

This invention is not considered to be constrained by prior art involving the formulation of microcarrier matrices from any of the presently proposed materials providing that the said materials were not previously recognized and documented in vivo as undergoing multiple endothelial binding and inducing rapid endothelial envelopment, and producing accelerated extravasation of macromolecules, microaggregates and microparticles in either the first microvascular bed encountered, or potentially (as proposed) semiselectively at foci of disease following systemic intravenous administration.

Endothelial-envelopment carriers may be formulated and stored in either the dry or fluid state, to which may be added, for example, pharmaceutically acceptable appropriate stabilizers, osmotic agents, colorings, flavorings, and physiologic solutions which render them appropriate for intravascular and intracavitary injection. The present invention is envisioned as most particularly applying to the vascular targeting phase of any future device (unavailable at present) which is developed for the efficient first-step transit across the external body barriers (e.g., gastrointestinal tract; oral, nasal rectal, bladder or vaginal mucosa; skin, cornea or sclera).

The following examples illustrate the invention described above.

EXAMPLE I

Preparation of Acetone-Stabilized and Heat-Stabilized heparin Microspheres and Molecular Microaggregates Beef lung heparin 100-200mg (152 units/mg, Upjohn Co.) was dissolved in 0.3-0.4 cc of distilled water and the solution emulsified in 6 cc of cottonseed oil (Sargent Welch, SC-11612) by vigorous vortex mixing for 1 to 5 minutes. This initial emulsion was added dropwise into 19 cc of stirred cottonseed oil which had been preheated to 114-122 C. This suspension was maintained at high temperature for 10 minutes and then allowed to cool to room temperature with continued stirring. (Alternatively, the heparin suspension was added dropwise into an identical volume of stirred cottonseed oil at 22 C. The oil suspensions were added dropwise into 30 cc (5 times the oil volume) of a mixture of 0.1% Tween 80 (Sigma Chemical Co.) in acetone in order to extract the oil phase (and to produce stable crystallization of the heparin in the unheated preparation). The microsphere-acetone suspensions were centrifuged at 1,250 × g for 5 minutes to sediment the spheres. The microspheres were extracted an additional 3 times with 0.1% Tween 80 in acetone (25 cc total volume or 4 times the oil volume). The resulting microspheres were either lyophilized to dryness or mixed thoroughly with 2% (w.v/) Tween 80 in 0.5 cc of acetone and allowed to air dry for 24 hours at 22 C. Both procedures gave heparin microspheres which were stable upon suspension in water or isotonic saline and had an average particle diameter of between 7 and 50 micrometers (um) as measured by light microscopy. The sizes depended on the duration of vortex mixing in the oil emulsification steps above.

Heparin microaggregates averaging 0.1 to 0.2 um in size were produced as described in the preceding steps, but with the addition of by sonicating the initial 6 cc of oil emulsion for 5 minutes at 20,000 Hz with a standard ultrasonifier and special microtip (Heat Systems, Inc.).

EXAMPLE 2

Preparation of Heparin Microspheres Containing Entrapped Amphotericin B a. Entrapment of amphotericin-cyclodextrin complex.

Amphotericin B, 20 mg without deoxycholate (E. R. Squibb and Sons, Inc.) and gamma cyclodextrin, 31 mg (Polysciences, Inc.) were dissolved at a 1:1 molar ratio in 0.4 cc of dimethyl sulfoxide (Sigma Chemical Co.). Beef lung heparin, 49 mg (as in Example 1) was dissolved in 0.8 cc of distilled water. The two solutions were mixed and then rapidly emulsified in 6 cc of cottonseed oil by vigorous and continuous vortex mixing. Aliquots were removed quickly (due to partial but controllable phase separation of the drug-cyclodextrin complex) and added dropwise to 0.1% Tween 80 in acetone according to the exact procedures described for the nonheated microsphere preparation of Example 1. The percentage of starting drug entrapped was 70% and the final drug content in spheres was 14% (w.w/). Resuspension in water and isotonic saline resulted in two size populations of particles, the major fraction (ca. 85% by mass) comprised larger microspheres, 7 to 25 um in diameter, and the smaller fraction (ca. 15% by mass) comprised smaller microspheres, 0.3 to 1.0 um in diameter. These two fraction were rapidly separable by micropore filtration. The larger spheres were observed microscopically to be packed with yellow-colored refractile granules which were similar in size to the smaller particles just described. Water suspensions of the lypohilized spheres (combined size fractions) were amenable to complete sedimentation by centrifugation. By colorometric assessment of the fraction of amphotericin B (yellow color) which sedimented with particles at incremental times after aqueous resuspension, the t ½ of controlled release for amphotericin B was approximately 3 days.

b. Entrapment of amphotericin B pre-emulsified with pluronic F68 block copolymer.

Native amphotericin B, 100 mg without deoxycholate (E. R. Squibb and Sons, Inc.) and 12 mg of the pluronic F68 block copolymer (polyoxypropylene-polyoxyethylene, Green Cross Corp.) were suspended in 1 cc of distilled water and ultrasonified for 1 minute (as in Example 1) to produce an initial emulsion with a particle size ranging from 0.1 to 5 um in diameter. This suspension was stirred overnight at 22 C in the dark, and then ultrasonified for an additional 1 minute. The resulting emulsion was significantly smaller, with a particle size ranging from 0.1 to 0.8 um in diameter. This emulsion was centrifuged at 500 × g for 2 minutes in order to sediment the larger (potentially uncoated) drug particles. The supernatant (fine emulsion, ca. 30-50% of the mass) was removed and used for subsequent entrapment in heparin microspheres. This was done by adding 70 mg of beef lung heparin (Upjohn Co., as in Example 1) to the 0.9 cc of recoverable supernatant (fine emulsion) stirring for 5 minutes to obtain complete solvation of the heparin, adding the resulting mixture to oil (preferably at room temperature, alternatively at 114-125 C. for 10 minutes, for extra stabilization), emulsifying it by vortexing, quickly stabilizing the emulsion by stirring into 0.1% Tween 80 in acetone at 22 C, and processing as described in Example 1. The resulting microspheres had an average diameter of 3-15 um depending on the duration of vortex mixing. As assessed colorimetrically, the percentage of drug entrapped was greater than 70% and the final drug content was 20-30% (w/w).

Parallel microspheres were made as described above, except with dextran T70 (Pharmacia Fine Chemicals) as the major matrix component and heparin as the surface coating (10% by weight). For these spheres, the surface coating was added as described in Example 3 below (starting at the text position marked "SURFACE COATING."

EXAMPLE 3

Preparation of Dextran T70 Microspheres with a Heparin Surface Coating of 10% by Weight Amphotericin B, 20 mg without deoxycholate (E. R. Squibb and Sons, Inc.) and gamma cyclodextrin, 30 mg were dissolved in 0.4 cc of dimethyl sulfoxide (Sigma Chemical Co.). Dextran T70 (Pharmacia Fine Chemicals), 49 mg was dissolved separately in 0.175 cc of dimethyl sulfoxide. The two aqueous suspensions were mixed and quickly emulsified in 7 cc of cottonseed oil (Sargent Welch, SC-11612). This oil suspension was added rapidly but dropwise to 0.1% Tween 80 in acetone (T-Ac), 35 cc. Microspheres were sedimented at 1250 × g for 5 minutes. The pellet was extracted one additional time with 10 cc of 0.1% T-Ac, resuspended in 0.5 cc of 2% T-Ac and allowed to dry for 45-60 minutes at 22 C (until no longer detectible). A surface coating was prepared as follows: Beef lung heparin (Upjohn Co., as above), 10 mg predissolved in 0.5 cc of distilled water, was added to the dried spheres. To this was added 6 cc of cottonseed oil (12 times the volume of water), and the suspension was emulsified by moderate vortex mixing, in order to apply the heparin coating to the surfaces of the previously crystallized dextran spheres. This emulsion was once again stabilized by dropwise addition to 30 cc of stirred 0.1% T-Ac, and the microspheres sedimented at 1250 × g for 5 minutes. Three additional extractions were performed with 10, 9, and 6 cc, respectively, of T-Ac. The pellet was resuspended in 0.5 cc of 2% T-Ac and allowed to air dry for 16 hours at 22 C. The percentage of drug entrapped was 65% and the final drug content was 12% by weight. Microsphere sizes ranged from 0.5 um to 30 um, depending on the duration of vortex mixing.

EXAMPLE 4

In Vitro Modification of Ulex Europaeus I Lectin Bound to Agarose Spheres

Ulex Europaeus I Lectin with affinity to endothelial factor VIII antigen, was obtained commercially (Vector Laboratories, Burlingame, Calif.) as a gel suspension in which the Ulex lectin was bound by a stable ether linkage, to agarose spheres (25075 um in diameter) of the lightly cross-linked polysaccharide comprising galactose plus 3,6-anhydrogalactose monomers). As obtained, the binding capacity was 2.5 mg of fucosyl glycoprotein per cc of gel and the suspension contained 10 mM fucose, the sugar hapten of highest specificity to saturate all Ulex binding sites.

a. Preparation for injection of spheres with hapten-blocked (fucose-bound) binding sites.

To 0.25 cc of the unwashed gel was added 0.75 cc of 0.2M phosphate-buffered 0.15N saline (Grand Island Biological Co.), in order to obtain a gel suspension which was sufficiently dilute for direct intravenous injection (below).

b. Preparation for injection of spheres with unblocked (available) binding sites.

The gel, 0.25 cc was washed 3 times by centrifugation at 2500 × g with 0.8 cc each of 0.02 M phosphate-buffered 0.15N saline, in order to remove almost all of the fucose sugar hapten which was initially bound to the Ulex binding lectin. The resulting pellet of spheres was suspended in a total volume of 0.8 cc for subsequent intravenous injection (below).

EXAMPLE 5

In Vivo Injection of Heparin Microspheres and Microaggregates Prepared as in Example 1

For all in vivo tests (this Example and Example 6 below), microspheres were suspended in phosphate-buffered saline (per Example 4) at a density such that their packed (centrifuged) volumes were 20 percent of their final volumes in suspension (spheres plus solution). Equivalent doses were given to each animal by injecting 0.125 cc of the fully suspended material. Lung targeting was accomplished by intravenous injection into CBA mice, and brain targeting was performed by carotid arterial injection into Sprague-Dawley rats. Analysis of organ targeting, envelopment and extravascular migration of spheres were carried out by 1) sacrificing representative test animals at 2, 5, 10, 15 and 20 minutes postinjection; fixing the brain tissue in 10% buffered formalin or inflating their lungs to a fixed size by injecting 10% Carson's buffered (pH 7.4) formalin intratracheally at a pressure equivalent to a 20-cm column of water; 2) processing the fixed tissue sections for light and electron microscopy; 3) staining these sections with hematoxylin and eosin (H & E), periodic acid Schiff (PAS), and reticulin histochemical stains; cutting (with a microtome) the light microscopic sections (below) at a 4-um thickness; and 5) analyzing morphometrically, the processed sections for the number and microscopic position of spheres in relation to vessels, perivascular structures, interstitium and airspaces of lung, and the microvessels pericyte (astrocyte) processes (which abut the microvessels of brain), and brain tissue proper.

The legend for all figures of tissue sections shown below are: M=microsphere; V=microvessel; A=airspace; e=endothelial membrane; and n=endothelial nucleus.

a. Injection of heparin microspheres (0.125 cc) intravenously and localization in CBA mouse lung.

FIG. 1 is a lung tissue section stained with PAS, which is representative of the test mice sacrificed 2-5 minutes after intravenous injection of the unheated, acetone-stabilized heparin microspheres of Example 1. At the center is a typical heparin microsphere (M) approximately 20 um in diameter, which has become lodged within the microvascular lumen of a lung capillary and is already completely enveloped by endothelial cell membrane (e), whose two nuclei (n) are present immediately adjacent and overlying the sphere. At the upper right-hand corner is an endothelial-coated microsphere (M) which has migrated partially out of its lung capillary (V) and is beginning to lose its endothelial coating (e, at 4-6 o'clock on the sphere) at position 8-9 o'clock on the sphere.

Figure 2:

FIG. 2 is a lung tissue section stained with PAS, which is representative of the test mice sacrificed 10 minutes after intravenous injection of the same heparin microspheres as in FIG. 1. At center is microsphere (M) the same heparin microspheres as in FIG. 1. At center is microsphere (M) which has migrated almost completely out of its lung capillary (V) into the adjacent airspace (A). Endothelial membrane (e) and nuclei (n) are still present on the microsphere surface. There minimal toxicity to the microvessel as evidenced by an absence of co-extravasted red blood cells or serum proteins (which would stain intensely with PAS). A second endothelial-coated and partially extravascular microsphere is present at lower right.

Smaller (nonembolizing) microspheres and microaggregates of all the heparin and heparin-coated formulations of Example 1 are observed to undergo similar envelopment and extravascular migration at approximately the same kinetics.

Table 1 summarizes the percentages and positions of intrapulmonary microspheres of 4 to 15-um diameters 15-20 minutes after intravenous injection:

TABLE 1

| Type of sphere | Approximate percentage of injected dose identified in lung | Percentage of spheres in extravascular locations |
|---|---|---|
| 1. Heparin (acetone) | 35 | 85 |
| 2. Heparin (heated) | 40 | 80 |

TABLE 1-continued

| Type of sphere | Approximate percentage of injected dose identified in lung | Percentage of spheres in extravascular locations |
|---|---|---|
| 3. Plain agarose* | 10 | 20 |

*Many of the remanent intravascular spheres were undergoing degradation due to serum amylase digestion, and only small fragments of these spheres could be identified.

These histologic and morphometric results document that the heparin microsphere surfaces induce rapid (less than 2 minutes) partial and/or complete endothelial coating which resulted in endothelial envelopment (walling-off) of the spheres, thereby functionally removing them from the vascular compartment (even during before they emigrate out of the vascular space). This slows intravascular degradation of the spheres and accelerates extravascular migration of the intact spheres (largely complete within 15 to 20 minutes), and greatly increases the proportion of spheres which become localized in the tissue (interstitial) compartment and airways.

Larger heparin microspheres (25-75 um diameters) experience pulmonary captures and extravascular migrations similar to those of the Ulex I spheres shown in Table 2 of Example 6, below.

b. Injection of heparin microspheres into the carotid artery and localization in Sprague-Dawley rat brain.

Heparin microspheres from Example 1 (0.250 cc, 5-15 um in diameter) were injected into the carotid artery and the rats sacrificed at 15 minutes. One to seven, small (0.2-3.0) PAS-positive particles were observed in and surrounding the microvessels of the cerebral and cerebellar cortex and the deep nuclei of the brain. Approximately 50% of the vessels were positive for emigrating particles. At 15 minutes postinjection, these particles were present largely along the processes of pericytes lying adjacent to the brain arterioles and capillaries. (Pericytes are thought to be involved in the transport of nutrients from the vessels into brain parenchma.) Smaller numbers of PAS-positive particles were identified at greater distances away from pericytes within the extracellular compartment of brain tissue proper. Morphometrically, at least 15 percent of the injected microspheres were localized in brain tissue at 15 minutes.

EXAMPLE 6

In Vivo Injection of Ulex Europaeus I Lectin Microspheres Prepare in Example 1

Ulex Europaeus I lectin microspheres (0.125 cc) were injected intravenously for localization in CBA mouse lung.

Figure 3:

FIG. 3 is a lung tissue section stained with PAS, which is representative of the test mice sacrificed 2-5 minutes after intravenous injection of the fucose-blocked, Ulex Europaeus agglutinin I-coated spheres of Example 4. A larger microsphere (M) is present (at left center) in the vascular space (V), which has undergone almost complete envelopment by endothelial membranes (e) and nuclei (n). A smaller microsphere (M) is present (at right center) which has undergone both endothelial envelopment and almost complete extravascular migration into the airspace (A). However, it remains attached to the basement membrane of the small vessel from which it emigrated. Remnants of endothelial membrane (e) still coat it at the surface of attachment but have been lost from the free surface. Histologic comparisons of heparin and Ulex I microspheres have revealed that a higher proportion of emigrated Ulex I spheres remain attached to the abluminal basement membrane, whereas a higher proportion of the heparin spheres (Example 5 above) have further migrated into distant structures, including lymphatics and airways. For all spheres, there was an absence of red blood cell attachment on the downstream surface, indicating that any tendency towards binding or agglutination of red cell surface blood-group substances had been successfully blocked by the sugar hapten Also, there was histologic evidence for the induction of acute coagulopathies or endothelial toxicity.

Figure 4:

FIG. 4 is a lung tissue section stained with a reticulin stain, which is representative of the test mice sacrificed at 10 minutes after intravenous injection of the identical fucose-blocked, Ulex Europaeus agglutinini-coated spheres of Example 3. At center, is a microsphere (M) which has undergone complete emigration from the vascular space (V) into the airspace (A), with continued attachment to the abluminal basement membrane. This sphere shows remanent coating by endothelial membranes (e,e) but uncoating on the opposite surface (u). Small fragments of reticulin (a connective tissue component of the vessel wall) have been carried through into the airspace with the microsphere (dark stringy material just below "A") but no red blood cells have been released from the vessels into the airspace. (Emigration of reticulin is not observed with emigration of the smallest, 10-um spheres present in this Ulex I suspension.) The microsphere of FIG. 4 is beginning to undergo degradation in the airspace at 10 minutes. At 20 minutes, the extent of degradation is only slightly greater that at 10 minutes for most of the extravastated sphere matrices (not shown). Examples 3 and 4 indicate that fucose-blocked Ulex I spheres undergo efficient uncoating upon contact with endothelial surfaces which have binding sites for the Ulex I lectin, and that this event induces endothelial envelopment and rapid extravascular migration of the spheres. Similar responses are seen for unblocked microspheres (with exposed Ulex I binding sites.) For smaller (nonembolizing) Ulex I spheres of 3-5 um diameters, such uncoating would be expected to occur preferentially in the microvessels supplying focal lesional tissues (involved by inflammation, infection and tumor).

Figure 5:

FIG. 5 is a lung tissue section stained with PAS, which is representative of the test mice sacrificed 20 minutes after intravenous injection of the identical fucose-blocked spheres of Examples 3 and 4. This exemplifies the rare intravascular microsphere (M) which can still be identified at 20 minutes. Although it has undergone nearly complete endothelial envelopment and partial extravascular migration, its migration is not yet complete. This rare example shows that the portion of the sphere which is most completely coated by endothelial membranes (e) is the most protected from intravascular amylase digestion and remains morphologically intact. Conversely, the portion of the sphere which is uncoated (the portion which invaginates most deeply into the vascular compartment "V") is has undergone morphologic fragmentation (f) and will shortly become completely digested within the vessel unless it first completes the process of emigration. This indicates that endothelial envelopment indeed renders the emigrating particles extravascular and hence protects them from digestion during the process of emigration. By the same process of walling off the particle, it can be inferred that most of the drug which is released in this newly formed endothelial pocket during microsphere emigration would also be walled off and released into the tissue compartment as the particle emerges on the tissue side. Note that blood flow has already been reestablished in this vessel at positions 5-7 o'clock around this sphere.

FIG. 6 is a representative example of control microsphere (Mc) of plain agarose which is present within a lung microvessel (V) 10 minutes after intravenous injection. In contrast to the Ulex I (and heparin) spheres, this sphere shows no evidence of endothelial coating on either the upstream or downstream free surfaces (u, uncoated). It also shows no evidence of beginning extravascular migration. A reticulin stain (not shown) indicates intact reticulin around all aspects of the vessel wall with which the sphere is in contact. Such control spheres (without Ulex I or heparin surfaces) migrate in a delayed (20 minutes or longer) inefficient manner (see Table 2 below), and undergo intravascular degradation with downstream release of microsphere fragments and drug.

Table 2 summarizes the percentages and positions of intrapulmonary microspheres of 25 to 75-um diameters at 10-20 minutes after intravenous injection:

TABLE 2

| Type of sphere | Approximate percentage of injected dose identified in lung | Percentage of spheres in extravascular locations |
| --- | --- | --- |
| 1. Ulex I, frucose blocked* | 90 | 80 |
| 2. Ulex I, unblocked* | 90 | 90 |
| 3. Plain agarose** | 10 | 20 |

*The higher lung-capture percentage of Ulex I versus the heparin spheres of Example 5, Table 1, is due to the larger diameters of these particles. Note, however, that plain agarose particles of the larger diameter (Table 2) are not effectively transported into the tissues, and hence, their capture percentage at 10-20 minutes is also low due to intravascular degradation and release from the lung. Smaller spheres with Ulex I surfaces would be expected to undergo capture percentages equivalent to heparin spheres of the same size.
**Many of the remanent intravascular spheres were undergoing degradation due to serum amylase digestion, and only small fragments of these spheres could be identified.

What is claimed is:

1. A composition comprising a multivalent binding agent surface which binds determinants of endothelial or epithelial cells;
   wherein the composition is a microsphere, microaggregate, or macromolecule less than about 250 micrometers in size, and has a matrix capable of containing a drug or diagnostic agent at a content of at least 12% (w/w); and
   wherein the multivalent binding agent surface consists of carbohydrate, oligosaccharide, monosaccharide, negatively charged polysaccharide, negatively charged oligosaccharide, dextran sulfate, glycosaminoglycan, heparin, heparin fragment, synthetic heparin analogue, heparan sulfate, dermatan sulfate, chondroitin sulfate, hyaluronic acid; and which induces rapid partial or total envelopment of said composition by endothelial or epithelial cells and facilitated migration across said cells into proximal tissues.

2. A composition comprising a multivalent binding agent surface which binds determinants of endothelial or epithelial cells;
   wherein the composition is a microsphere, microaggregate, or macromolecule less than about 250 micrometers in size, and has a matrix capable of containing a drug or diagnostic agent at a content of at least 12% (w/w); and
   wherein the multivalent binding agent is a heparin, a heparin fragment, or synthetic heparin analogue, which induces rapid partial or total envelopment of said composition by endothelial or epithelial cells and facilitated migration across said cells into proximal tissues.

3. A composition comprising a multivalent binding agent surface which binds determinants of endothelial or epithelial cells;
   wherein the composition is a microsphere, microaggregate, or macromolecule less than about 250 micrometers in size, and has a matrix capable of containing a drug or diagnostic agent at a content of at least 12% (w/w); and
   wherein the multivalent binding agent consists essentially of heparin, heparin fragment, synthetic heparin analogue, heparan sulfate, dermatan sulfate, chondroitin sulfate, hyaluronic acid or dextran sulfate, which induces rapid partial or total envelopment of said composition by endothelial or epithelial cells and facilitated migration across said cells into proximal tissues.

4. The composition of claim 1 defined further as consisting of microparticles or microaggregates coated with heparins which bind to complementary substances present on endothelium or epithelium, said complementary substances including heparan sulfates and antithrombin III.

5. The composition of claim 1 wherein the multivalent binding agent surface coating is reversibly blocked by a chemical moiety that renders the multivalent binding agent initially covert and wherein the reversibly blocking chemical moiety is susceptible to release by triggering agents including lowered pH, altered temperature, contact with normal or abnormal endothelia or epithelia, altered enzyme levels, degradative enzymes, radiofrequency energy, ultrasound, magnetism or electricity.

6. The composition of claim 1 wherein the drug or diagnostic agent is a drug active against microorganisms.

7. The composition of claim 6 wherein the drug or diagnostic agent is an antifungal agent.

8. The composition of claim 1 wherein the drug or diagnostic agent is a drug active against tumor cells.

9. The composition of claim 1 wherein the drug or diagnostic agent is a drug active in treating biological lesions which involve activated or diseased endothelium or subendothelial molecules or structures.

10. The composition of claim 1 wherein the carrier comprises one or more of macromolecules, microaggregates, microparticles, microspheres, and microemulsions.

11. The composition of claim 1 wherein the multivalent binding agent surface binds to laminin, collagen, fibronectin or fibronectin fragments.

* * * * *